(12) United States Patent
Ebert et al.

(10) Patent No.: US 8,591,783 B2
(45) Date of Patent: Nov. 26, 2013

(54) MEDICAL DEVICES WITH ENCAPSULATED VISIBILITY PARTICLES

(75) Inventors: Michael J. Ebert, Fridley, MN (US); Steven L. Waldhauser, White Bear Township, MN (US); Mark D. Schneider, Mound, MN (US); Gregory P. Shipe, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 909 days.

(21) Appl. No.: 12/609,620

(22) Filed: Oct. 30, 2009

(65) Prior Publication Data

US 2010/0130962 A1 May 27, 2010

Related U.S. Application Data

(60) Provisional application No. 61/117,198, filed on Nov. 23, 2008.

(51) Int. Cl.
*A61M 25/098* (2006.01)
*B05D 7/00* (2006.01)

(52) U.S. Cl.
USPC ............... 264/171.28; 427/2.3; 427/220

(58) Field of Classification Search
USPC ............... 264/279.1, 177.2, 171.28; 604/529; 427/2.3, 220
See application file for complete search history.

(56) References Cited

U.S. PATENT DOCUMENTS

| | | | |
|---|---|---|---|
| 4,689,250 A * | 8/1987 | Quella et al. | 427/216 |
| 5,300,048 A | 4/1994 | Drewes, Jr. et al. | |
| 5,431,956 A * | 7/1995 | Robb et al. | 427/220 |
| 5,702,373 A | 12/1997 | Samson | |
| 5,908,413 A | 6/1999 | Lange et al. | |
| 6,106,473 A * | 8/2000 | Violante et al. | 600/458 |
| 6,641,776 B1 | 11/2003 | Weaver et al. | |
| 6,905,458 B2 | 6/2005 | Choay et al. | |
| 7,065,394 B2 | 6/2006 | Hobot et al. | |
| 7,713,259 B2 | 5/2010 | Gosiengfiao et al. | |
| 2004/0224001 A1 * | 11/2004 | Pacetti et al. | 424/423 |
| 2006/0074401 A1 | 4/2006 | Ross | |
| 2008/0058919 A1 * | 3/2008 | Kramer-Brown et al. | 623/1.34 |
| 2010/0130963 A1 | 5/2010 | Ebert et al. | |

FOREIGN PATENT DOCUMENTS

| | | | |
|---|---|---|---|
| WO | WO 2005/035043 A2 | 4/2005 | |
| WO | WO 2005/035043 A3 | 6/2005 | |
| WO | WO 2005/051435 A2 | 6/2005 | |
| WO | WO 2005/051435 A3 | 7/2006 | |
| WO | WO 2010/059408 A2 | 5/2010 | |
| WO | WO 2010/059409 A2 | 5/2010 | |

OTHER PUBLICATIONS

"How to choose a Poly Tarp (Polyethylene Tarpaulin)" by CreativeShelters.com; 4 pages.*
International Search Report and Written Opinion for PCT application No. PCT/US2009/062769, Oct. 14, 2010; 13 pgs.

* cited by examiner

*Primary Examiner* — Joseph S Del Sole
*Assistant Examiner* — Kimberly A Stewart
(74) *Attorney, Agent, or Firm* — Carol F. Barry

(57) ABSTRACT

The preparation and use of medical devices having radiopaque and echogenic materials including coated tungsten and/or tungsten carbide particles are disclosed herein.

22 Claims, 1 Drawing Sheet

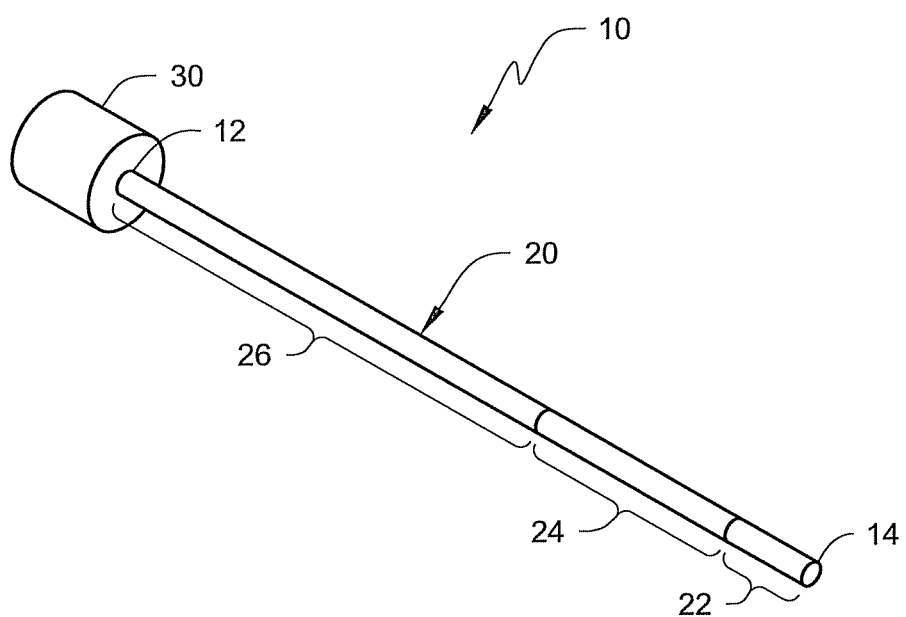

MEDICAL DEVICES WITH ENCAPSULATED VISIBILITY PARTICLES

This application claims the benefit of U.S. Provisional Application Ser. No. 61/117,198, filed Nov. 23, 2008, which is herein incorporated by reference in its entirety.

TECHNICAL FIELD

The present disclosure relates generally to medical devices and, more particularly, to medical devices that include selected segments that are visible using both fluoroscopy and ultrasonic imaging.

BACKGROUND

It may be desirable to monitor the position of medical devices such as, e.g., catheters, while they are within a patient's body. For example, it may be useful to monitor the position of guide catheters which are used to place catheters, electrode leads and the like in desired locations within the body of a patient. A guide catheter typically includes an elongated sheath that is inserted into a blood vessel or another portion of the body. A catheter or lead is introduced through an inner channel defined by the sheath.

To enable precise positioning of a medical device, one or more selected segments may include visibility materials that are visible under fluoroscopy and/or ultrasonic imaging. Using fluoroscopic or ultrasonic imaging techniques, the physician can visualize the guide catheter, and place the catheter or electrode lead in a desired position. Guide catheters, for example, may incorporate radiopaque and/or echogenic materials to promote visibility.

BRIEF DESCRIPTION OF THE VIEWS OF THE DRAWING

The present disclosure will be further described with reference to the figures of the drawing, wherein:

FIG. 1 is a perspective view of one exemplary medical device in the form of a catheter.

DETAILED DESCRIPTION OF EXEMPLARY EMBODIMENTS

The present disclosure is directed to medical devices (such as, e.g., catheters, guide catheters, etc.) that include one or more selected segments that are constructed using visibility materials compounded with one or more polymeric materials that make the selected segments visible using both fluoroscopy and ultrasonic imaging. The visibility material may take the form of tungsten and/or tungsten carbide particles dispersed within a polymeric material.

The use of visibility material as described herein can potentially promote enhanced visibility of a medical device (such as a guide catheter) using both fluoroscopic and ultrasonic imaging techniques. This feature provides a physician with flexible imaging options. The medical device can be used by physicians who prefer fluoroscopic imaging, for example, as well as those who prefer ultrasound. In each case, the physician may select the same guide catheter without regard to the desired imaging modality.

In some embodiments, the use of a visibility material that is both echogenic and radiopaque as an additive to enable both fluoroscopic and ultrasonic imaging can potentially allow the overall additive level to be lower, which may tend to preserve the mechanical properties of a composite blend incorporating the visibility material.

In some instances, a reduced amount of visibility material in a composite blend may also enhance the slittability of the guide catheter. In this manner, the visible material can potentially be loaded into polymeric material in amounts that promote visibility while maintaining slittability.

Although it is known that polyether block amides can be loaded with tungsten and/or tungsten carbide to provide visibility using both fluoroscopy and ultrasonic imaging, these compositions can, in some instances, suffer from degradation during aging. The degradation can adversely impact the flexibility and other mechanical properties of the segments in which the visibility materials are provided. The approaches to providing the visible medical device segments as described herein may address these aging issues while still retaining a suitable or enhanced level of visibility using both fluoroscopic and ultrasonic imaging.

In one embodiment, the present disclosure provides a medical device that includes a radiopaque and echogenic material, wherein the radiopaque and echogenic material includes coated tungsten and/or tungsten carbide particles distributed within a base polymeric material (i.e., a first polymeric material) including a polyether block amide. The particles can be coated with a coating material selected from the group consisting of additional polymeric material (i.e., a second polymeric material), ceramic material, metal, metal oxides, and combinations thereof. The medical device can be in the form of a guide catheter including an elongated sheath having a proximal end and a distal tip, and at least a portion of the distal tip and/or elongated sheath includes the radiopaque and echogenic material. Methods of preparing such medical devices are also provided.

In another embodiment, the present disclosure provides a method of increasing the shelf life of at least a portion of a medical device. In certain embodiments, the method includes: providing a base polymeric material (i.e., a first polymeric material); and distributing coated tungsten and/or tungsten carbide particles within the base polymeric material, wherein the coated particles include an additional polymeric coating material (i.e., a second polymeric material) that is more hydrophobic than the base polymeric material. In other embodiment, the method includes providing a base polymeric material (i.e., a first polymeric material); and distributing coated tungsten and/or tungsten carbide particles within the base polymeric material, wherein the coated particles include a coating material that is a substantial barrier to the transmission of water and/or water vapor.

The above brief description of the disclosure is not intended to describe each embodiment or every implementation of the present disclosure. Rather, a more complete understanding of the disclosure will become apparent and appreciated by reference to the following description and claims in view of the accompanying FIGURE of the drawing.

In the following detailed description of illustrative embodiments of the present disclosure, reference is made to the accompanying FIGURE of the drawing which form a part hereof, and in which are shown, by way of illustration, specific embodiments that may be practiced. It is to be understood that other embodiments may be utilized and structural changes may be made without departing from the scope of the present disclosure.

FIG. 1 is a perspective view of one medical device that may be used in connection with the present disclosure which is in the form of a catheter 10. As shown in FIG. 1, catheter 10 includes a proximal end 12, distal tip 14, and an elongated sheath 20 extending between the proximal and distal ends. Catheter 10 may be sized for insertion into a lumen, such as a blood vessel, within the human body. Catheter 10 preferably defines at least one inner channel (not shown in FIG. 1) through which other elements such as other catheters, electrode leads, etc. may be inserted. A handle 30 may be coupled to proximal end 12 of catheter 10. A slitter (not shown) may be positioned near proximal end 12, e.g., adjacent handle 20 if the catheter 10 is to be slit during removal of the catheter 10.

The sheath 20 of the catheter 10 may include any number of segments, with the sheath 10 including three segments 22, 24, and 26 disposed along the length of catheter 10. Sheath 20 may be formed to provide either a straight or pre-bent shape to catheter 10, depending on the desired end application.

Sheath 20 may be manufactured using materials that promote maneuverability and that may also permit slitting along the length of catheter 10. In particular, each segment 22, 24, and 26 of the sheath 20 may be constructed of one or more polymeric materials, such as polyether block amide, nylon block polymer, silicone, or polyurethane, as well as composites or mono-polymers. An example of one potentially suitable group of polymeric materials that can be used are polyether block amides marketed under the trademark PEBAX and commercially available from Arkema, Inc. (Philadelphia, Pa.).

In some embodiments, the sheath may also include other components such as, e.g., reinforcing braids, etc. If a reinforcing braid is provided, it may terminate short of the distal segment 22 such that the flexibility of the sheath 16 is higher within at least the distal segment 22 as compared to the portions of the sheath 16 that do include a reinforcing braid. Examples of some sheath constructions including reinforcing braids or strands are described in, e.g., U.S. Pat. No. 7,065,394 (Hobot et al.).

Medical devices of the present disclosure, such as catheter 10, are constructed to exhibit properties that enhance visibility of selected portions of the medical device when using fluoroscopic or ultrasonic imaging techniques. With reference to FIG. 1, distal segment 22 is found at the distal tip of catheter 10 and incorporates visibility material that makes the segment 22 visible using both fluoroscopy and ultrasonic imaging modalities. The visibility material also may be provided in other segments and/or along the entire length of the catheter.

Each sheath segment 22, 24, and 26 may, in some embodiments, be constructed from a similar material with a similar concentration of tungsten and/or tungsten carbide particles. However, the different sheath segments may be manufactured with polymeric materials that have different hardness characteristics. It may be preferred that the distal segment 22 be flexible such that the distal end of the catheter 10 is more flexible than the segments 24 and 26 such that that tip 14 of the catheter 10 is relatively atraumatic. As a particular illustration, sheath segments 22, 24, and 26 may be constructed from PEBAX material with 25, 35, and 55 Shore D hardnesses, respectively. In another illustration, each sheath segment 22, 24, and 26 may be independently constructed from PEBAX material having a desired hardness (e.g., 25, 35, 40, 55, 63, 70, or 72 Shore D hardness). In one embodiment, the tungsten and/or tungsten carbide particles can be added to selected sheath segments 22, 24, and 26 in concentrations that do not significantly degrade the overall mechanical properties of sheath 20, e.g. on the order of about 60 to about 90 percent by weight. In another embodiment, the tungsten and/or tungsten carbide particles can be added to selected sheath segments 22, 24, and 26 in concentrations on the order of about 60 to about 85 percent by weight. In still yet another embodiment, the tungsten and/or tungsten carbide particles can be added to selected sheath segments 22, 24, and 26 in concentrations on the order of about 60 to about 80 percent by weight. In another embodiment, the tungsten and/or tungsten carbide particles can be added to selected sheath segments 22, 24, and 26 in concentrations on the order of about 65 to about 80 percent by weight. In another embodiment, the tungsten and/or tungsten carbide particles can be added to selected sheath segments 22, 24, and 26 in concentrations on the order of about 65 to about 75 percent by weight.

As one particular example, the tungsten and/or tungsten carbide particles may be added to the base polymeric material in sheath segment 22 in the amount of about 70 to about 75 percent by weight and, more preferably, about 73 to about 74 percent by weight. In an exemplary embodiment, the jet milled tungsten carbide material is added to the polymeric material in a weight of about 73.2 percent by weight. A concentration of 73.2 percent by weight tungsten carbide particles to PEBAX material corresponds to a concentration of about 15 percent by volume. Barium sulfate particles may be added to sheath segments 24 and 26 in the amount of about 20 to about 40 percent by weight and, more preferably, about 30 percent by weight.

If the catheter 10 is a guide catheter that is to be slit or torn along its length during use, the addition of tungsten and/or tungsten carbide particles may offer exceptional echogenicity and, when added to the polymeric material, permit ready slitting along the length of catheter 10. As a result, it may be desirable to balance the degree of echogenicity against the slittability of sheath 20. As more tungsten and/or tungsten carbide particles are added to segments 22, 24, and 26, the material forming the sheath 20 becomes difficult to process and, in some cases, difficult to maneuver for insertion into and removal from the body of a patient.

Although polyether block amides can be loaded with tungsten and/or tungsten carbide particles to provide visibility using both fluoroscopy and ultrasonic imaging, it has been discovered that, in some instances, these compositions can potentially suffer from degradation due to temperature (e.g., oxidation) and/or humidity (e.g., hydrolysis). The degradation can adversely impact the flexibility and other properties of the segments in which the visibility materials are provided.

Coated particles of tungsten and/or tungsten carbide can be added to polyether block amide to provide the desired visibility, and in some embodiments, the degradation due to temperature and/or humidity can be substantially reduced as compared to medical devices in which the particles are not coated. The tungsten and/or tungsten carbide particles can be coated with a wide variety of coating materials including, for example, additional polymeric material, ceramic material, metal, metal oxides, and combinations thereof. In certain embodiments, the coating material can be less reactive than the tungsten and/or tungsten carbide particles. In certain embodiments, the coating material can have barrier properties (e.g., function as a substantial barrier to the transmission of water and/or water vapor). In certain embodiments, the coating material can be more hydrophobic than the base polymeric material (e.g., a polyether block amide), also referred to as the first polymeric material. The coating material can have a high or a low surface area.

In certain embodiments, the coated tungsten and/or tungsten carbide particles can have a coating that includes an additional polymeric material (also referred to as the second polymeric material) different from the base polymeric material (e.g., polyether block amide material). In certain embodiments, the additional polymeric material is more hydrophobic than the base polymeric material (e.g., a polyether block amide). A wide variety of polymers can be used as the additional polymeric material. In certain embodiments, the additional polymeric material is a thermoplastic material. Examples of polymers that can be used as the additional polymeric material include, but are not limited to, polyolefins (e.g., polyethylene and/or polypropylene), fluoropolymers, polycarbonates, polyurethanes, polyesters, polyester ethers, higher durometer polyether block amides, and combinations thereof. In certain embodiments, the softening temperature (e.g., melt temperature or glass transition temperature) of the additional polymeric material can be lower than the softening temperature of the base polymeric material. In certain embodiments, the softening temperature (e.g., melt temperature or glass transition temperature) of the additional polymeric material can be the same as or higher than the softening temperature of the base polymeric material. The coated tungsten and/or tungsten carbide particles can be prepared by a wide variety of methods. For example, the additional polymeric material can be coated onto tungsten and/or tungsten carbide particles using melt coating, solvent coating, dispersion coating, deposition coating, dip coating, other coating methods, or combinations thereof.

In certain embodiments, the coated tungsten and/or tungsten carbide particles can have a coating that includes a ceramic material. A wide variety of ceramic materials can be used to coat the tungsten and/or tungsten carbide particles. Exemplary ceramic materials include, but are not limited to, titanium ceramics (e.g., titanium dioxide and/or titanium nitride), hydroxylapatite, zirconium ceramics (e.g., zirconia), aluminum oxide, calcium phosphate, and combinations thereof. The coated tungsten and/or tungsten carbide particles can be prepared by a wide variety of methods. For example, ceramic material can be coated onto tungsten and/or tungsten carbide particles using thermal chemical vapor deposition (CVD), plasma enhanced CVD, sputtering (e.g., RF sputtering), aerosol deposition, nanoparticle deposition, other coating methods, or combinations thereof.

In certain embodiments, the coated tungsten and/or tungsten carbide particles can have a coating that includes a metal. A wide variety of metals can be used to coat the tungsten and/or tungsten carbide particles. Exemplary metals include, but are not limited to, gold, silver, palladium, titanium, iridium, and combinations thereof. The coated tungsten and/or tungsten carbide particles can be prepared by a wide variety of methods. For example, metal can be coated onto tungsten and/or tungsten carbide particles using electrochemical deposition, physical vapor deposition, thermal/cold sprays, nanoparticle deposition, thermal chemical vapor deposition (CVD), plasma enhanced CVD, sputtering (e.g., RF sputtering), other coating methods, or combinations thereof.

In certain embodiments, the coated tungsten and/or tungsten carbide particles can have a coating that includes a metal oxide. The coated tungsten and/or tungsten carbide particles can be prepared by a wide variety of methods. For example, metal oxides can be coated onto tungsten and/or tungsten carbide particles using electrochemical deposition, physical vapor deposition, thermal/cold sprays, nanoparticle deposition, thermal chemical vapor deposition (CVD), plasma enhanced CVD, sputtering (e.g., RF sputtering), dispersion coating, solvent coating, dip coating, sintering, other coating methods, or combinations thereof.

In certain embodiments, the tungsten and/or tungsten carbide particles can have an average diameter of less than about 1000 nanometers (where particle size refers generally to a diameter or width of the particles, although spherical particles are not necessarily required). In other embodiments, the tungsten and/or tungsten carbide particles can have an average diameter of less than about 500 nanometers. In yet other embodiments, the tungsten and/or tungsten carbide particles can have an average diameter of less than about 750 nanometers. In some embodiments, the tungsten and/or tungsten carbide particles may be formed by jet milling. In some embodiments, additional polymeric material coating the tungsten and/or tungsten carbide particles can have a thickness of about 5 micrometers to about 1000 micrometers. In some embodiments, ceramic material coating the tungsten and/or tungsten carbide particles can have a thickness of about 10 nanometers to about 1000 micrometers. In some embodiments, metal coating the tungsten and/or tungsten carbide particles can have a thickness of about 10 nanometers to about 1000 micrometers. In some embodiments, metal oxides coating the tungsten and/or tungsten carbide particles can have a thickness of about 10 nanometers to about 1000 micrometers.

The coated tungsten and/or tungsten carbide particles can be incorporated into a polyether block amide composition by a wide variety of suitable methods. For example, the coated tungsten and/or tungsten carbide particles and polyether block amide beads can be fed directly to an extruder, with the extrudate having the coated tungsten and/or tungsten carbide particles incorporated into the polyether block amide. Alternatively, a masterbatch of the coated tungsten and/or tungsten carbide particles incorporated into the polyether block amide at higher loadings can be prepared using, for example, suitable melt processing methods (e.g., using extruders, mills, or internal mixers), and the desired amount of the masterbatch of coated tungsten and/or tungsten carbide particles can be fed to the extruder with the polyether block amide beads.

Although described primarily in connection with the distal segment 22, the tungsten and/or tungsten carbide particles can be incorporated along the length of catheter 10 in sheath segments 24 and 26 as well as 22. In particular, the tungsten and/or tungsten carbide particles can be dispersed in polymeric material that is molded or extruded to form the entire sheath 20. Alternatively, the tungsten and/or tungsten carbide particles may be provided in sheath segment 22 in distal tip 14, with the remaining sheath segments 24 and 26 carrying barium sulfate particles to enhance visibility of those portions of the catheter 10. Essentially, any selected portion of the sheath 20 may incorporate the coated tungsten and/or tungsten carbide particles as needed to provide enhanced visibility.

Accordingly, methods of increasing the shelf life of at least a portion of a medical device are also provided herein. For example, coated tungsten and/or tungsten carbide particles can be added to (and preferably distributed within) a base polymeric material (e.g., polyether block amides, polyurethanes, polyesters, polyester ethers, polycarbonates, polyolefins, and combinations thereof). In preferred embodiments, the medical devices that include the coated tungsten and/or tungsten carbide particles can have increased shelf life in comparison to comparable medical devices including uncoated tungsten and/or tungsten carbide particles. In certain embodiments, the coated particles include tungsten and/or tungsten carbide particles coated with an additional polymeric material (e.g., polyolefins such as polyethylene and/or polypropylene, fluoropolymers, polycarbonates, polyurethanes, polyesters, polyester ethers, higher durometer polyether block amides, and combinations thereof) that is more hydrophobic (e.g., have a higher contact angle with water) than the base polymeric material.

ALTERNATIVE/ADDITIONAL APPROACHES: In addition, one or more of the following approaches may be used as an alternative to the use of coated particles or in conjunction with coated particles to further increase the shelf life of the medical device.

Tungsten particles (as opposed to tungsten carbide particles) can be selected as a visibility material. Tungsten particles may have a reduced tendency to effect degradation (e.g., less catalytic filler) than tungsten carbide particles.

Polyurethane (as opposed to polyether block amide) can be selected as the base polymeric material in which the coated particles are dispersed. In some instances, the polyurethane may be limited to the portion of the medical device (e.g., catheter) that incorporates the visibility material. Polyurethanes can be more hydrolytically stable than, for example, polyether block amides.

Tungsten carbide and/or tungsten particles can be used as the visibility material in a higher durometer polyether block amide (e.g., such as those available under the trade designation PEBAX MX 1205 polyether block amides from Arkema), with the loading level of the visibility material reduced to offset the higher durometer of the polymeric material such that the resulting composite material retains selected mechanical properties, e.g., still provides an atraumatic tip.

One or more additives can be used to enhance stability by reducing hydrolysis and/or oxidation. The additives may include one or more of antioxidants (e.g., a peroxide decomposer such as IRGAFOS 168; a non-polar anti-oxidant such as IRGANOX 1098; metal deactivators such as IRGANOX MD-1024; etc.); anti-hydrolysis agents (e.g., carbodiimides such as, e.g., CARBAXOL, etc.); etc.

The medical device can be sterilized using ethylene oxide or other sterilization methodologies, and the sterile pouch can be placed into a bag that is impervious to moisture and/or oxygen. Optionally, this bag can be back filled with a dry (inert) gas, such as nitrogen, argon, and the like, and then the bag can be sealed. In another embodiment, the medical device pouch can be placed into a bag that is impervious to moisture and/or oxygen, a dessicant can be added to adsorb any moisture present in the bag, and then the bag can be sealed. For example, the medical device can be sterilized and placed in a moisture proof package that includes added dessicant, the package can be purged with a dry (inert) gas, and the package sealed. For embodiments in which at least a portion of the medical device includes a hydrophilic polymer, the bag can be purged with a humidified gas such that the relative humidity is less than or equal to about 30 percent to prevent unnecessary drying of the hydrophilic polymer.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this disclosure are discussed and reference has been made to possible variations within the scope of this disclosure. These and other variations and modifications in the disclosure will be apparent without departing from the scope of the disclosure, and it should be understood that this disclosure is not limited to the illustrative embodiments set forth herein. Accordingly, the disclosure is to be limited only by the claims provided below and equivalents thereof.

What is claimed is:

1. A method of preparing at least a portion of a medical device, the method comprising:
   providing a base polymeric material comprising a polyether block amide; and
   distributing a plurality of discrete coated particles within the base polymeric material, wherein the coated particles comprise tungsten and/or tungsten carbide particles coated with an additional polymeric material that is more hydrophobic than the base polymeric material, and wherein the polymeric coating has a thickness of about 5 micrometers to about 1000 micrometers.

2. The method of claim 1 wherein distributing further comprises:
   providing tungsten and/or tungsten carbide particles; and
   coating the tungsten and/or tungsten carbide particles with the additional polymeric material to provide the coated particles.

3. The method of claim 1 wherein the device is in the form of a guide catheter comprising an elongated sheath having a proximal end and a distal tip, and at least a portion of the distal tip and/or elongated sheath comprises the coated particles.

4. A method of increasing the shelf life of at least a portion of a medical device, the method comprising:
   providing a base polymeric material; and
   distributing a plurality of discrete coated tungsten and/or tungsten carbide particles within the base polymeric material, wherein the coated particles comprise an additional polymeric coating material that is more hydrophobic than the base polymeric material, wherein the polymeric coating has a thickness of about 5 micrometers to about 1000 micrometers, and
   wherein incorporating the coated particles provides at least a portion of the medical device that has increased shelf life.

5. The method of claim 4 wherein the base polymeric material is selected from the group consisting of polyether block amides, polyurethanes, polyesters, polyester ethers, polycarbonates, polyolefins, and combinations thereof.

6. The method of claim 5 wherein the additional polymeric material is selected from the group consisting of polyolefins, fluoropolymers, polycarbonates, polyurethanes, polyesters, polyester ethers, higher durometer polyether block amides, and combinations thereof.

7. The method of claim 4 further comprising forming a layer that is more resistant to hydrolysis than the base polymeric material over at least a portion of the medical device.

8. The method of claim 4 wherein the base polymeric material further comprises one or more antioxidants and/or anti-hydrolysis agents.

9. The method of claim 4 wherein the device is in the form of a guide catheter comprising an elongated sheath having a proximal end and a distal tip, and at least a portion of the distal tip and/or elongated sheath comprises the coated tungsten and/or tungsten carbide particles.

10. A method of increasing the shelf life of at least a portion of a medical device, the method comprising:
    providing a base polymeric material; and
    distributing a plurality of discrete coated tungsten and/or tungsten carbide particles within the base polymeric material, wherein the coated particles comprise a coating material that comprises an additional polymeric material having a substantial barrier to the transmission of water vapor and/or water, and wherein the polymeric coating has a thickness of about 5 micrometers to about 1000 micrometers.

11. The method of claim 10 wherein the base polymeric material is selected from the group consisting of polyether block amides, polyurethanes, polyesters, polyester ethers, polycarbonates, polyolefins, and combinations thereof.

12. The method of claim 10 wherein the additional polymeric material is selected from the group consisting of polyolefins, fluoropolymers, polycarbonates, polyurethanes, polyesters, polyester ethers, higher durometer polyether block amides, and combinations thereof.

13. The method of claim 10 further comprising forming a layer that is more resistant to hydrolysis than the base polymeric material over at least a portion of the medical device.

14. The method of claim 10 wherein the base polymeric material further comprises one or more antioxidants and/or anti-hydrolysis agents.

15. The method of claim 10 wherein the device is in the form of a guide catheter comprising an elongated sheath having a proximal end and a distal tip, and at least a portion of the distal tip and/or elongated sheath comprises the coated tungsten and/or tungsten carbide particles.

16. A method of preparing at least a portion of a medical device, the method comprising:
providing a first polymeric material, wherein the first polymeric material comprises a polyether block amide; and
distributing a plurality of discrete coated particles within the first polymeric material, wherein the coated particles comprise tungsten and/or tungsten carbide particles coated with a second polymeric material that is more hydrophobic than the first polymeric material, and wherein the polymeric coating has a thickness of about 5 micrometers to about 1000 micrometers.

17. A method of increasing the shelf life of at least a portion of a medical device, the method comprising:
providing a first polymeric material; and
distributing a plurality of discrete coated tungsten and/or tungsten carbide particles within the first polymeric material, wherein the coated particles comprise a second polymeric coating material that is more hydrophobic than the first polymeric material, and wherein the polymeric coating has a thickness of about 5 micrometers to about 1000 micrometers,
wherein incorporating the coated particles provides at least a portion of the medical device that has increased shelf life.

18. The method of claim 17 wherein the first polymeric material is selected from the group consisting of polyether block amides, polyurethanes, polyesters, polyester ethers, polycarbonates, polyolefins, and combinations thereof.

19. The method of claim 18 wherein the second polymeric material is selected from the group consisting of polyolefins, fluoropolymers, polycarbonates, polyurethanes, polyesters, polyester ethers, higher durometer polyether block amides, and combinations thereof.

20. A method of increasing the shelf life of at least a portion of a medical device, the method comprising:
providing a first polymeric material; and
distributing a plurality of discrete coated tungsten and/or tungsten carbide particles within the first polymeric material, wherein the coated particles comprise a coating material that comprises a second polymeric material having a substantial barrier to the transmission of water and/or water vapor, and wherein the polymeric coating has a thickness of about 5 micrometers to about 1000 micrometers.

21. The method of claim 20 wherein the first polymeric material is selected from the group consisting of polyether block amides, polyurethanes, polyesters, polyester ethers, polycarbonates, polyolefins, and combinations thereof.

22. The method of claim 20 wherein the second polymeric material is selected from the group consisting of polyolefins, fluoropolymers, polycarbonates, polyurethanes, polyesters, polyester ethers, higher durometer polyether block amides, and combinations thereof.

* * * * *